United States Patent
Leveillard et al.

(10) Patent No.: US 10,668,129 B2
(45) Date of Patent: Jun. 2, 2020

(54) SYNERGISTIC COMBINATION OF NEURONAL VIABILITY FACTORS AND USES THEREOF

(71) Applicants: INSERM (INSTITUT NATIONAL DE LA SANTÉ ET DE LA RECHERCHE MÉDICALE), Paris (FR); CENTRE NATIONAL DE LA RECHERCHE SCIENTIFIQUE-CNRS, Paris (FR); UNIVERSITE PIERRE ET MARIE CURIE (PARIS 6), Paris (FR); THE REGENTS OF THE UNIVERSITY OF CALIFORNIA, Oakland, CA (US); THE TRUSTEES OF THE UNIVERSITY OF PENNSYLVANIA, Philadelphia, PA (US)

(72) Inventors: Thierry Leveillard, Paris (FR); John Flannery, Berkeley, CA (US); Xin Mei, Paris (FR); Leah Byrne, Berkeley, CA (US); José-Alain Sahel, Paris (FR); Emmanuelle Clerin-Lachapelle, Paris (FR); Junwei Sun, Philadelphia, PA (US); Jean Bennett, Philadelphia, PA (US); Jeannette Bennicelli, Philadelphia, PA (US)

(73) Assignees: INSERM (INSTITUT NATIONAL DE LA SANTE ET DE LA RECHERCHE MEDICALE), Paris (FR); CENTRE NATIONAL DE LA RECHERCHE SCIENTIFIQUE—CNRS, Paris (FR); UNIVERSITE PIERRE ET MARIE CURIE (PARIS 6), Paris (FR); THE REGENTS OF THE UNIVERSITY OF CALIFORNIA, Oakland, CA (US); THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 148 days.

(21) Appl. No.: 15/576,027

(22) PCT Filed: May 20, 2016

(86) PCT No.: PCT/EP2016/061488
§ 371 (c)(1),
(2) Date: Nov. 21, 2017

(87) PCT Pub. No.: WO2016/185037
PCT Pub. Date: Nov. 24, 2016

(65) Prior Publication Data
US 2018/0153962 A1   Jun. 7, 2018

(30) Foreign Application Priority Data

May 21, 2015   (WO) ................ PCT/IB2015/000967

(51) Int. Cl.
| | | |
|---|---|---|
| A61K 38/17 | (2006.01) | |
| A61P 27/02 | (2006.01) | |
| C07K 14/47 | (2006.01) | |
| C12N 15/86 | (2006.01) | |
| A61K 48/00 | (2006.01) | |

(52) U.S. Cl.
CPC .......... *A61K 38/1709* (2013.01); *A61P 27/02* (2018.01); *C07K 14/47* (2013.01); *C12N 15/86* (2013.01); *A61K 48/00* (2013.01); *C12N 2750/14143* (2013.01); *C12N 2750/14171* (2013.01)

(58) Field of Classification Search
CPC ................................................ A61K 38/1709
See application file for complete search history.

(56) References Cited

U.S. PATENT DOCUMENTS

2014/0328821 A1* 11/2014 Luo ...................... C12N 9/0051
424/94.4

FOREIGN PATENT DOCUMENTS

| JP | 2015-501156 A | 1/2015 |
|---|---|---|
| WO | 02/081513 A2 | 10/2002 |
| WO | 2008/148860 A1 | 12/2008 |
| WO | 2014/060517 A1 | 4/2014 |

OTHER PUBLICATIONS

Byrne et al. (Investigative Ophthalmology & Visual Science Mar. 2012, vol. 53, 1907. ARVO Annual Meeting Abstract. Mar. 2012. "AAV-Mediated Delivery of RdCVF and RdCVFL in a Mouse Model of Retinal Degeneration") (Year: 2012).*
Vandenberghe et al. (PLOS ONE; Jan. 2013; 8(1): e53463, pp. 1-7). (Year: 2013).*
Byrne et al., "Viral-mediated RdCVF and RdCVFL expression protects cone and rod photoreceptors in retinal degeneration", Journal of Clinical Investigation, Nov. 21, 2014, pp. 105-116, vol. 125, No. 1.
Elachouri et al., "Thioredoxin rod-derived cone viability factor protects against photooxidative retinal damage", Free Radical Biology and Mediciine, Jan. 14, 2015, pp. 22-29, vol. 81.

(Continued)

*Primary Examiner* — Scott Long
(74) *Attorney, Agent, or Firm* — W&C IP

(57) ABSTRACT

The present invention relates to the synergistic combination of the short and long Rod-Derived Cone Viability Factors and to methods for treating retinal degenerative diseases.

Figure 1:
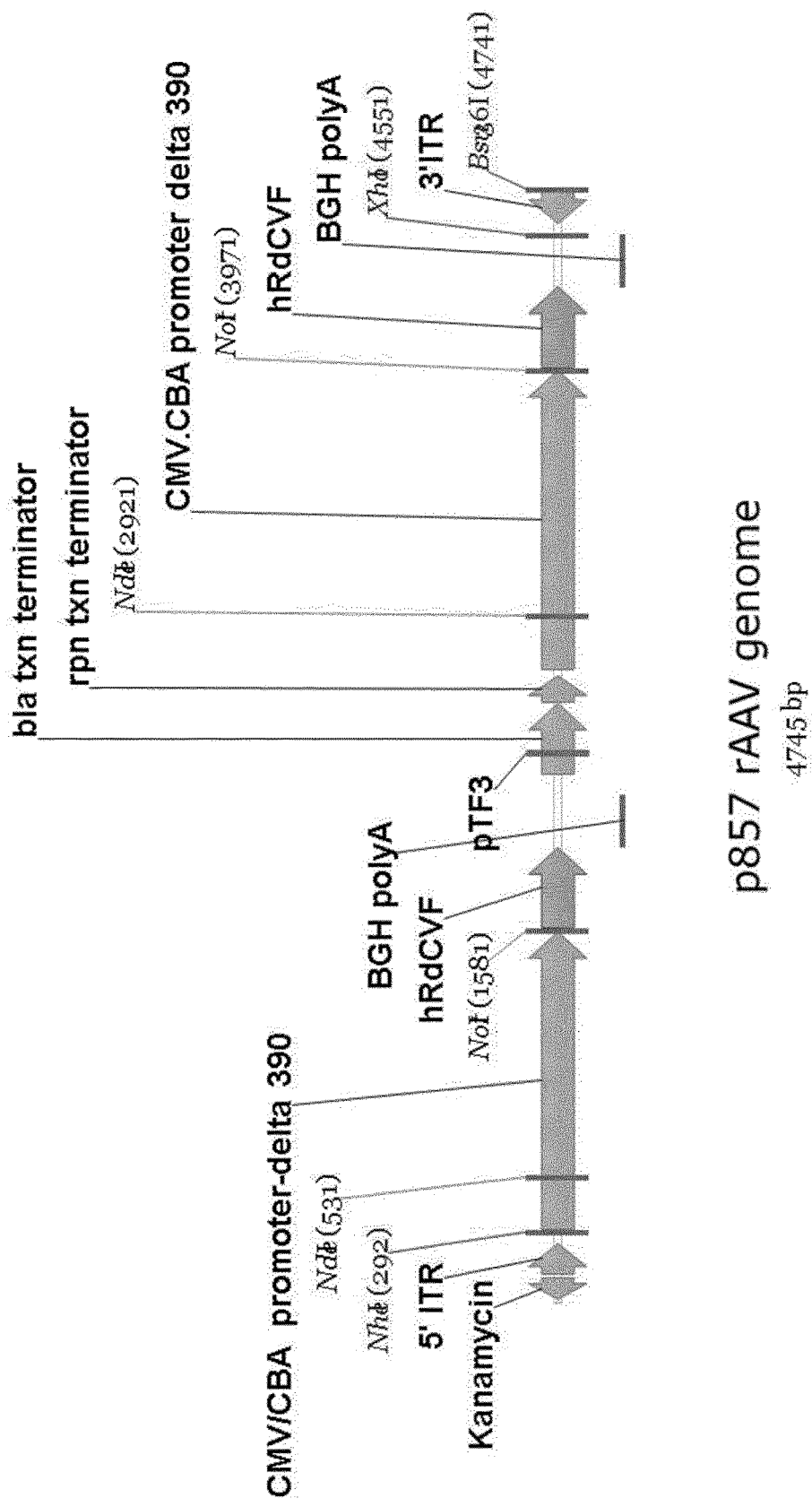

5 Claims, 4 Drawing Sheets
Specification includes a Sequence Listing.

(56) References Cited

OTHER PUBLICATIONS

Xin et al., "The Thioredoxin Encoded by the Rod-Derived Cone Viability Factor Gene Protects Cone Photoreceptors Against Oxidative Stress", Antioxidants & Redox Signaling, Jun. 1, 2016, pp. 909-923, vol. 24, No. 16.
Byrne et al: "AAV-mediated Delivery of Rod-derived Cone Viability Factor in a Mouse Model of Retinal Degeneration", IOVS May 2011.
Sahel et al: "Functional rescue of cone photoreceptors in retinitis pigmentosa", Graefe's Archive for Clinical and Experimental Ophthalmology, vol. 231, pp. 1669-1677, Apr. 11, 2013.

\* cited by examiner

SEQUENCE LISTING

```
<160> NUMBER OF SEQ ID NOS: 2

<210> SEQ ID NO 1
<211> LENGTH: 109
<212> TYPE: PRT
<213> ORGANISM: Homo sapiens

<400> SEQUENCE: 1

Met Ala Ser Leu Phe Ser Gly Arg Ile Leu Ile Arg Asn Asn Ser Asp
1               5                   10                  15

Gln Asp Glu Leu Asp Thr Glu Ala Glu Val Ser Arg Arg Leu Glu Asn
            20                  25                  30

Arg Leu Val Leu Leu Phe Phe Gly Ala Gly Ala Cys Pro Gln Cys Gln
        35                  40                  45

Ala Phe Val Pro Ile Leu Lys Asp Phe Phe Val Arg Leu Thr Asp Glu
    50                  55                  60

Phe Tyr Val Leu Arg Ala Ala Gln Leu Ala Leu Val Tyr Val Ser Gln
65                  70                  75                  80

Asp Ser Thr Glu Glu Gln Gln Asp Leu Phe Leu Lys Asp Met Pro Lys
                85                  90                  95

Lys Trp Leu Phe Leu Pro Phe Glu Asp Asp Leu Arg Arg
            100                 105

<210> SEQ ID NO 2
<211> LENGTH: 212
<212> TYPE: PRT
<213> ORGANISM: Homo sapiens

<400> SEQUENCE: 2

Met Ala Ser Leu Phe Ser Gly Arg Ile Leu Ile Arg Asn Asn Ser Asp
1               5                   10                  15

Gln Asp Glu Leu Asp Thr Glu Ala Glu Val Ser Arg Arg Leu Glu Asn
            20                  25                  30

Arg Leu Val Leu Leu Phe Phe Gly Ala Gly Ala Cys Pro Gln Cys Gln
        35                  40                  45
```

```
Ala Phe Val Pro Ile Leu Lys Asp Phe Phe Val Arg Leu Thr Asp Glu
 50              55                  60
Phe Tyr Val Leu Arg Ala Ala Gln Leu Ala Leu Val Tyr Val Ser Gln
 65              70                  75                   80
Asp Ser Thr Glu Glu Gln Gln Asp Leu Phe Leu Lys Asp Met Pro Lys
             85                  90                  95
Lys Trp Leu Phe Leu Pro Phe Glu Asp Asp Leu Arg Arg Asp Leu Gly
            100                 105                 110
Arg Gln Phe Ser Val Glu Arg Leu Pro Ala Val Val Val Leu Lys Pro
            115             120                 125
Asp Gly Asp Val Leu Thr Arg Asp Gly Ala Asp Glu Ile Gln Arg Leu
130                     135                 140
Gly Thr Ala Cys Phe Ala Asn Trp Gln Glu Ala Ala Glu Val Leu Asp
145                 150                 155                 160
Arg Asn Phe Gln Leu Pro Glu Asp Leu Glu Asp Gln Glu Pro Arg Ser
                165                 170                 175
Leu Thr Glu Cys Leu Arg Arg His Lys Tyr Arg Val Glu Lys Ala Ala
            180                 185                 190
Arg Gly Gly Arg Asp Pro Gly Gly Gly Gly Glu Glu Gly Gly Ala
            195             200                 205
Gly Gly Leu Phe
210
```

SYNERGISTIC COMBINATION OF NEURONAL VIABILITY FACTORS AND USES THEREOF

FIELD OF THE INVENTION

The present invention relates to neurodegenerative disorders, and more particularly to a pharmaceutical composition for treating and/or preventing neurodegenerative disorders.

BACKGROUND OF THE INVENTION

Neurodegenerative disorder encompasses a range of seriously debilitating conditions that are characterized by neuron degeneration.

Rod-cone dystrophies, such as retinitis pigmentosa (RP), are genetically heterogeneous retinal degenerative diseases characterized by the progressive death of rod photoreceptors followed by the consecutive loss of cones. RP is one of the most common forms of inherited retinal degeneration, affecting around 1:3,500 people worldwide (1). Over 54 mutations causing RP have been identified to date with the majority of these mutations in rod-specific transcripts. RP patients initially present with loss of vision under dim-light conditions as a result of rod dysfunction, with relative preservation of macular cone-mediated vision. As the disease progresses, however, the primary loss of rods is followed by cone degeneration, and a deficit in corresponding cone-mediated vision. In modern society, in which much of the environment is artificially lit, and many activities rely on high acuity color vision, retention of cone-mediated sight in RP patients would lead to a significant improvement in quality of life.

The loss of cones in RP subsets caused by rod-specific mutations is poorly understood, although several mechanisms, which are not necessarily mutually exclusive, have been proposed. Some hypothesized mechanisms implicate a 'neighbor effect' whereby cone death is a consequence of the release of endotoxins from the degeneration of surrounding rods, or as a result of the loss of contact with rods, retinal pigment epithelium (RPE) or Müller glia. Alternatively, activation of Müller cells and the release of toxic molecules may play a role. Another hypothesis is that the quantities of oxygen or retinoids delivered to the photoreceptor layer by the RPE from the choroidal blood circulation are excessive and toxic as the metabolic load of rods is lost (2). Punzo et al. showed evidence that in murine models of retinal degeneration cones die in part as a result of starvation and nutritional imbalance, driven by the insulin/mammalian target of rapamycin pathway (3). Additionally, it has been suggested that the loss of a survival factor secreted by rods and required for cone survival may contribute to cone loss (4, 5).

In agreement with the last hypothesis, transplanted healthy retinal tissue has been shown to support cone survival in areas distant from the grafted tissue in the rd1 mouse (6, 7).

International patent application WO2008/148860A1 describes a family of trophic factors, called rod-derived cone viability factor (RdCVF) and RdCVF2 that are able to increase neuron survival and are useful for treating and/or preventing neurodegenerative disorders such as RP.

The rod-derived cone viability factor (RdCVF) was originally identified from a high-throughput method of screening cDNA libraries as a candidate molecule responsible for this rescue effect (4). Rods secrete RdCVF, and therefore, as rods die, the source of this paracrine factor is lost and RdCVF levels decrease. The loss of expression of RdCVF, and secreted factors like it, may therefore contribute to the secondary wave of cone degeneration observed in rod-cone dystrophies. RdCVF has been shown to mediate cone survival both in culture (8) and when injected subretinally in mouse and rat models of recessive and dominant forms of retinitis pigmentosa (4, 9). Disruption of Nxnl1, the gene encoding RdCVF, renders mouse photoreceptors increasingly susceptible to photoreceptor dysfunction and cone loss over time (10).

Nxnl1 codes for two isoforms of RdCVF through differential splicing. The isoform mediating cone survival is a truncated form of its longer counterpart, RdCVFL, which includes a C-terminal extension conferring enzymatic function (11). RdCVFL, which contains all the amino acids of RdCVF, is encoded by exons 1 and 2 of the Nxnl1 gene and is a member of the thioredoxin family (12). Thioredoxins have diverse functions, including maintaining the proper reducing environment in cells and participating in apoptotic pathways. These functions are accomplished via thioloxidoreductase reactions mediated by a conserved CXXC catalytic site within a thioredoxin fold (13).

However, there is still a need for additional neuroprotective treatments for neurodegenerative disorders.

SUMMARY OF THE INVENTION

The inventors have surprisingly found that, by combining the short (RdCVF) and long isoforms (RdCVFL) of the NXNL1 gene, a synergistic effect could be obtained.

Hence, the present invention relates to a method for treating a patient suffering from a retinal degenerative disease comprising the step consisting of administering to said patient a therapeutically effective amount of a first nucleic acid encoding a short isoform of the NXNL1 gene, Rod-derived Cone Viability Factor (RdCVF) and of a second nucleic acid encoding a long isoform of the NXNL1 gene, RdCVFL.

Said short and long isoform may be administered by separate vectors or by a single vector.

Accordingly, in one aspect, the present invention also relates to an expression vector comprising a first nucleic acid encoding a short isoform of Rod-derived Cone Viability Factor (RdCVF) and a second nucleic acid encoding a long isoform of RdCVF.

In another aspect, the present invention also relates to a kit-of-parts for use in a method for treating a degenerative disorder of the photoreceptors comprising:

a first expression vector comprising a first nucleic acid encoding a short isoform Rod-derived Cone Viability Factor (RdCVF) and a second expression vector comprising a second nucleic acid encoding a long isoform RdCVFL.

DETAILED DESCRIPTION OF THE INVENTION

The present invention relates to a method for treating a patient suffering from a retinal degenerative disease comprising the step consisting of administering to said patient a therapeutically effective amount of a first nucleic acid encoding a short isoform Rod-derived Cone Viability Factor (RdCVF) and of a second nucleic acid encoding a long isoform RdCVF.

Said short and long isoform may be administered by separate vectors or by a single vector.

Accordingly, in a first aspect, the present invention relates to a method for treating a patient suffering from a retinal degenerative disease comprising the step consisting of administering to said patient a therapeutically effective amount of a first nucleic acid encoding a short isoform Rod-derived Cone Viability Factor (RdCVF) and of a second nucleic acid encoding a long isoform RdCVFL, wherein said first nucleic acid and said second nucleic acid are contained in a single expression vector.

The present invention also relates to an expression vector comprising a first nucleic acid encoding a short isoform Rod-derived Cone Viability Factor (RdCVF) and a second nucleic acid encoding a long isoform RdCVFL.

As used herein, the term Rod-derived Cone Viability Factor (RdCVF) refers to the protein encoded by the thioredoxin-like 6 (Txnl6) or Nucleoredoxin-like 1 (NXNL1) gene. It encompasses the RdCVF proteins of any animal species. Typically, the RdCVF proteins according to the present invention can be a mammalian RdCVF proteins, including, but not limited to mice, rats, cats, dogs, non-human primates and human.

Unless otherwise specified, the term "RdCVF" refers to the short isoform of the NXNL1 gene and "RdCVFL" or "adCVF-L" the long isoform of the NXNL1 gene.

Typically, in mice, the short isoform (RdCVF) is a 109 amino-acid long protein references under Uniprot accession number Q91W38. The murine long isoform (RdCVF-L) is a 217 amino-acid long protein referenced under Q8VC33.

In one embodiment of the invention, the short isoform of RdCVF is the human short isoform of RdCVF (hRdCVF), having the following sequence:

```
                                              (SEQ ID No. 1)
         10           20           30           40
MASLFSGRIL IRNNSDQDEL DTEAEVSRRL ENRLVLLFFG 50           60           70           80
AGACPQCQAF VPILKDFFVR LTDEFYVLRA AQLALVYVSQ 90          100          109
DSTEEQQDLF LKDMPKKWLF LPFEDDLRR
```

In one embodiment of the invention, the long isoform of the NXNL1 gene is the human long isoform RdCVFL (hRdCVFL), having the sequence referenced under accession number Q96CM4 and set forth below:

```
                                              (SEQ ID No. 2)
         10           20           30           40
MASLFSGRIL IRNNSDQDEL DTEAEVSRRL ENRLVLLFFG 50           60           70           80
AGACPQCQAF VPILKDFFVR LTDEFYVLRA AQLALVYVSQ 90          100          110          120
DSTEEQQDLF LKDMPKKWLF LPFEDDLRRD LGRQFSVERL 130          140          150          160
PAVVVLKPDG DVLTRDGADE IQRLGTACFA NWQEAAEVLD 170          180          190          200
RNFQLPEDLE DQEPRSLTEC LRRHKYRVEK AARGGRDPGG

210
GGGEEGGAGG LF
```

The sequences of the RdCVF and RdCVFL proteins are described in Chalmel et al. 2007, BMC Molecular Biology 2007, 8:74 and in the international patent application WO2008/148860.

As used herein, the terms "vector" and "expression vector" are used interchangeably to refer to an expression vector. The expression vector according to the invention may be in the form of a plasmid, a virus, a phage etc.

Typically, the expression vector according to the present invention can be a virus.

In one embodiment, the expression vector is an adeno-associated vector (AAV).

AAVs have been extensively described in the art as suitable vectors for gene delivery. Indeed, AAVs are non-pathogenic and display a broad range of tissue specificity. Typically, AAVs according to the present invention are AAVs that are able to target retinal cells.

Examples include, but are not limited to, AAV2, AAV2/8, AAV9, and AAV7m8. In one embodiment, the AAV according to the present invention is obtained according to the method described in international patent application WO2012/158757.

Typically, the first and second nucleic acids, encoding respectively the short and long isoform of the NXNL1 gene, are under the control of a promoter that allows the expression of said short and long isoform in the target cells. Suitable promoters can be ubiquitous promoters, such as the CMV promoter.

Suitable promoters can be promoters that enable the expression in the retina, preferably in retinal pigmented epithelial cells and photoreceptor cells.

In one embodiment, the promoter allows gene expression in retinal pigmented epithelial cells.

In one embodiment, the promoter allows gene expression in cone photoreceptors. An non-limiting example is the opsin promoter.

Typically, the short isoform of the NXNL1 gene is expressed at least by retinal pigmented epithelial cells and the long isoform is expressed at least by cone photoreceptor cells.

In the context of the invention, the term "treating" or "treatment", as used herein, means reversing, alleviating, inhibiting the progress of, or preventing the disorder or condition to which such term applies, or one or more symptoms of such disorder or condition (e.g., retinal degenerative diseases).

The term "retinal degenerative diseases" encompasses all diseases associated with cone degeneration. retinal degenerative disease include but are not limited to Retinitis Pigmentosa, age-related macular degeneration, Bardet-Biedel syndrome, Bassen-Kornzweig syndrome, Best disease, choroidema, gyrate atrophy, Leber congenital amaurosis, Refsum disease, Stargardt disease or Usher syndrome.

In one embodiment of the invention, the retinal degenerative disease is Retinitis Pigmentosa.

According to the invention, the term "patient" or "patient in need thereof" is intended for a human or non-human mammal affected or likely to be affected with retinal degenerative diseases.

According to the present invention, a "therapeutically effective amount" of a composition is one which is sufficient to achieve a desired biological effect, in this case increasing the neuron viability. It is understood that the effective dosage will be dependent upon the age, sex, health, and weight of the recipient, kind of concurrent treatment, if any, frequency of treatment, and the nature of the effect desired. However, the preferred dosage can be tailored to the individual subject, as is understood and determinable by one of skill in the art, without undue experimentation.

The expression vector of the invention can be suitable for intravenous administration or intraocular administration. In a particular embodiment, the expression vector is administered by intravitreal injection.

In one aspect, the invention also relates to a pharmaceutical composition comprising an expression vector comprising a first nucleic acid encoding a short isoform of the NXNL1 gene, Rod-derived Cone Viability Factor (RdCVF) and a second nucleic acid encoding a long isoform of the NXNL1 gene, RdCVF-L, and a pharmaceutically acceptable carrier.

Without wishing to be bound by theory, it is believed that the delivery of the short isoform RdCVF and of the long isoform RdCVF-L leads to a synergistic effect.

On the one hand, the short isoform RdCVF is produced and secreted by the retinal pigmented epithelium (RPE), protecting the cones by stimulating aerobic glycolysis through the RdCVF receptor at the cell surface of the cones by a non-cell autonomous mechanism.

On the other hand, the long isoform, RdCVFL, protects the cones against oxidative damage in a cell autonomous manner, due to its thioloxidoreductase function.

In another aspect of the invention, the short and long isoforms RdCVF and RdCVF-L are administered by separate vectors, which can be administered simultaneously or sequentially.

Therefore, the present invention also relates to a method for treating a patient suffering from a retinal degenerative disease comprising the step of administering to said patient a therapeutically effective amount of a first nucleic acid encoding a short isoform RdCVF and of a second nucleic acid encoding a long isoform RdCVF-L, wherein said first nucleic acid and second nucleic acid are contained in separate expression vectors.

The invention also relates to a kit-of-parts for use in a method for treating a degenerative disorder of the photoreceptors comprising:
a first expression vector comprising a first nucleic acid encoding a short isoform of the NXNL1 gene, Rod-derived Cone Viability Factor (RdCVF) and
a second expression vector comprising a second nucleic acid encoding a long isoform of the NXNL1 gene, RdCVF-L.

The invention will be further illustrated through the following examples and figures.

FIGURES LEGENDS

Figure 2:
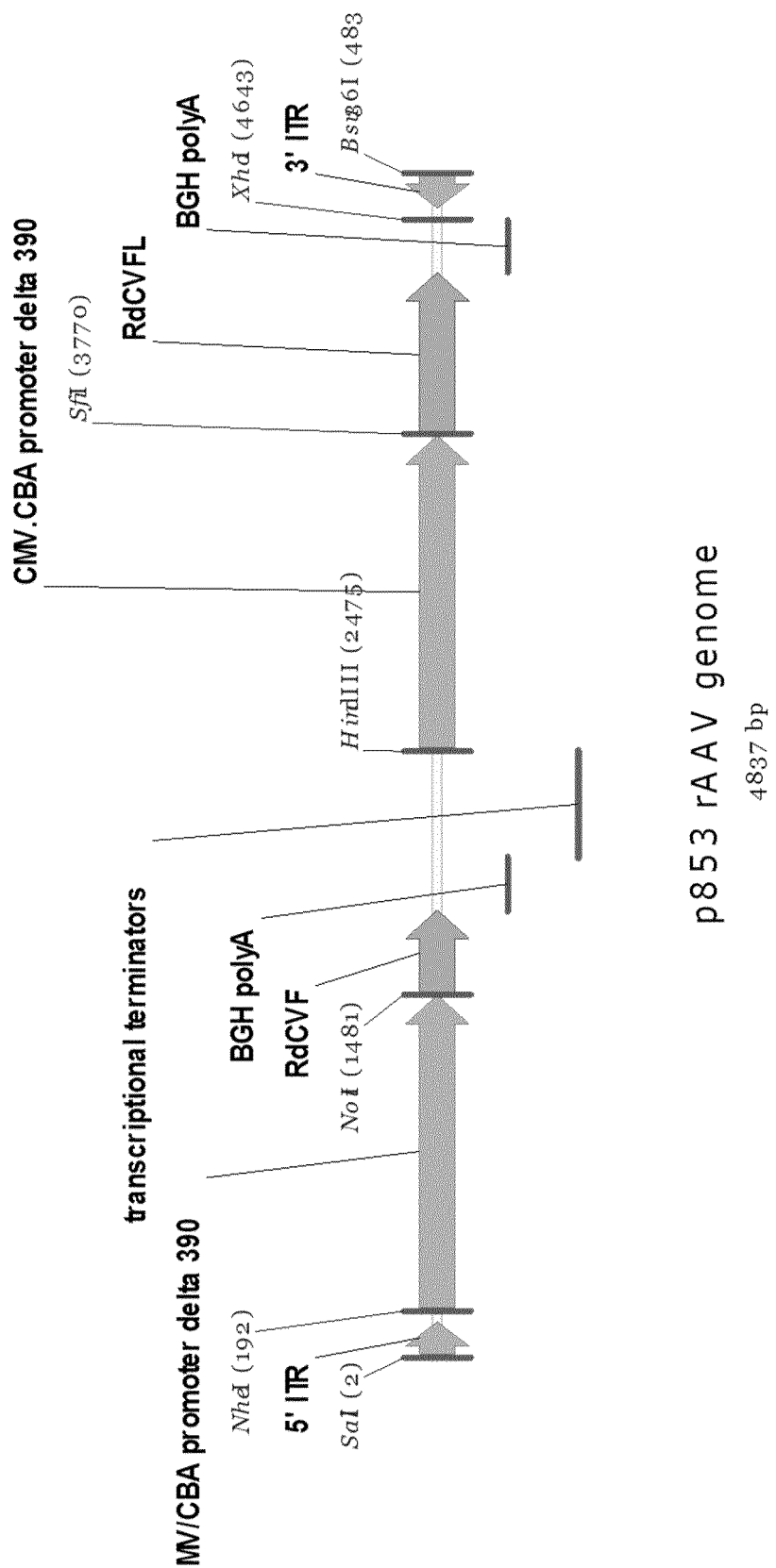

FIG. 1: schematic representation of the 2×RdCVF vector (plasmid p857 and AAV CT-39)
Kanamycin: Plasmid selection in bacteria
5' ITR AAV invert terminal repeat
CMV/CBA promoter-delta 390: Mixed cytomegalovirus/chicken beta actin (ubiquitous and strong promoter)
hRdCVF: human RdCVF cDNA
BGH polyA: Stabilization of mRNA
pTF3, bla txn terminator, rpn txn terminator: set of transcriptional terminators and an insulator, located external to 3"ITR in the plasmid (i.e. not in the rAAV genome). pTF3 is embedded in the bla txn.
CMV/CBA promoter-delta 390 Mixed cytomegalovirus/chicken beta actin (ubiquitous and strong promoter)
hRdCVF: human RdCVF cDNA
BGH polyA: Stabilization of mRNA
3' ITR AAV invert terminal repeat
FIG. 2: schematic representation of the RdCVF-RdCVFL vector (plasmid p853 and AAV CT-35)

Figure 3:
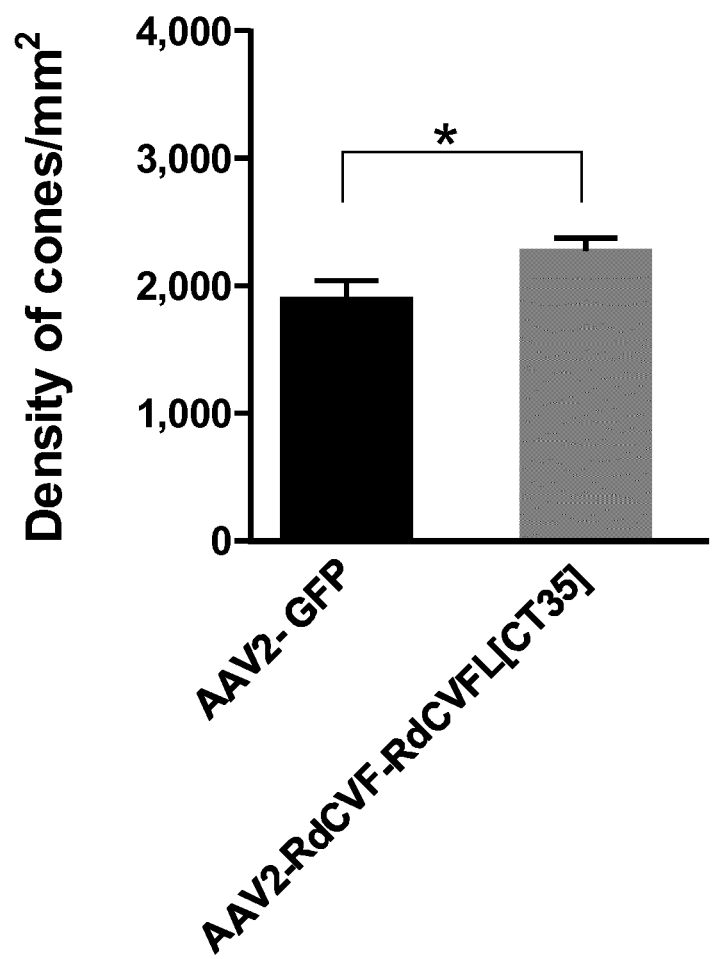

The vector contains the following elements Kanamycin: Plasmid selection in bacteria 5' ITR AAV invert terminal repeat
CMV/CBA promoter-delta 390 Mixed cytomegalovirus/chicken beta actin (ubiquitous and strong promoter)
hRdCVF: human RdCVF cDNA
BGH polyA: Stabilization of mRNA
pTF3, bla txn terminator, rpn txn terminator: set of transcriptional terminators and an insulator, located external to 3"ITR in the plasmid (i.e. not in the rAAV genome). pTF3 is embedded in the bla txn.
CMV/CBA promoter-delta 390: Mixed cytomegalovirus/chicken beta actin (ubiquitous and strong promoter)
hRdCVFL: human RdCVFL cDNA
BGH polyA: Stabilization of mRNA
3' ITR AAV invert terminal repeat FIG. 3: Density of cones (PN44) after sub-retinal injection of the rd1 mouse (PN14) of AAV2-GFP versus AAV2RdCVF/RdCVFL [CT35]

Figure 4:
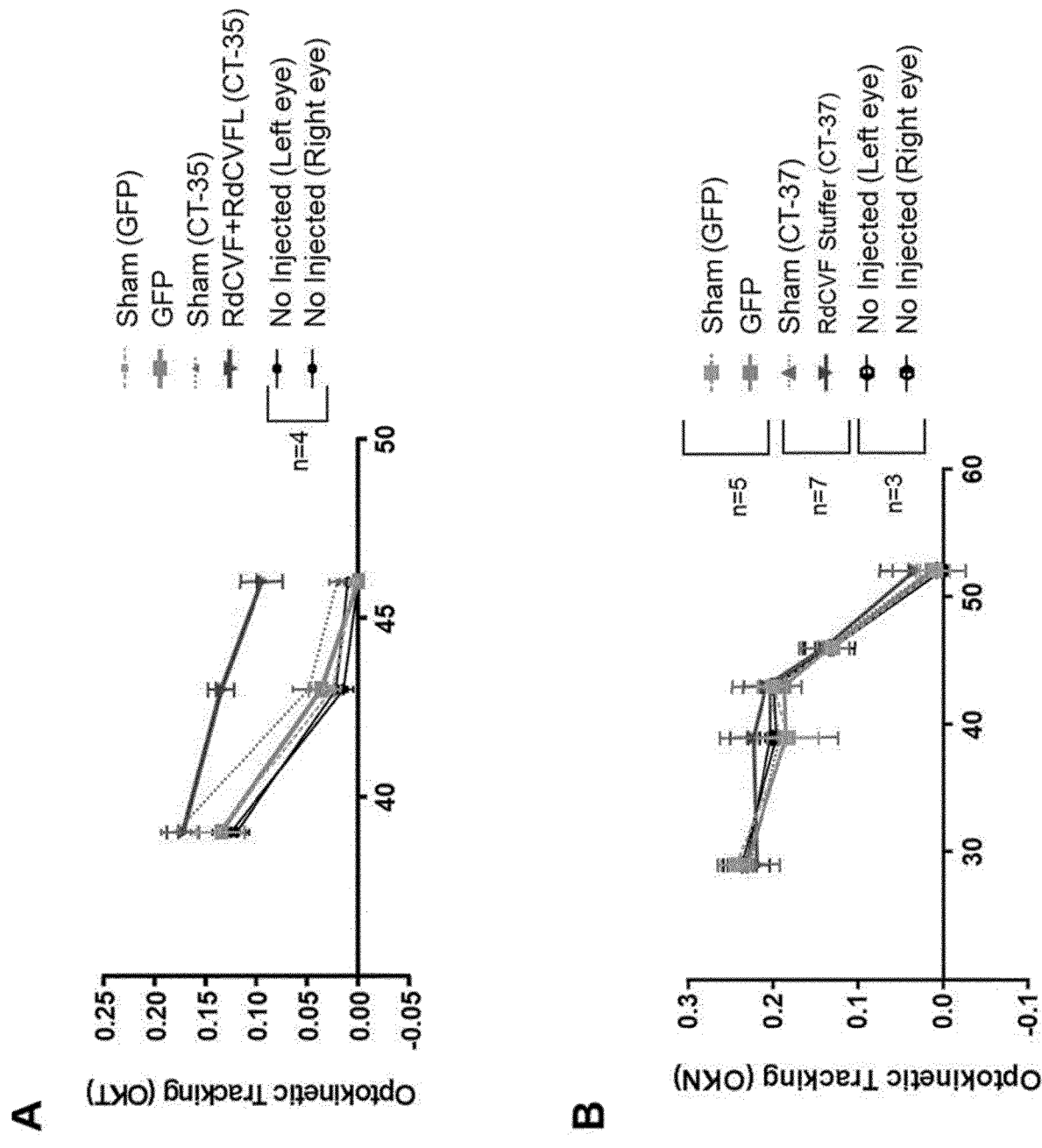

FIG. 4: Visual acuity of the rd10 mouse after subretinal injection of AAV2RdCVF/RdCVFL [CT35] (FIG. 4A) vs AAV2RdCVF [CT37] (FIG. 4B)

EXAMPLES

Example 1: AAV-RdCVF Rescues Cones and AAV-RdCVFL Protects Rods in Retinal Degeneration Example 1 corresponds to the experimental data published by the inventors in the following publication:

Byrne L C, Dalkara D, Luna G, Fisher S K, Clérin E, Sahel J A, Léveillard T, Flannery J G., J Clin Invest., 2015 January; 125(1):105-16. doi: 10.1172/JCI65654. Epub 2014 Nov. 21. "Viral-mediated RdCVF and RdCVFL expression protects cone and rod photoreceptors in retinal degeneration." (32 in the list of references below)

The inventors describe experiments that study the bifunctional nature of the Nxnl1 gene by evaluating the effects of expression of the two RdCVF isoforms, RdCVF and RdCVFL, via gene transfer in the rd10 mouse, a well-characterized model of rod-cone dystrophy resulting from a mutation in the β-subunit of PDE6, the rod-specific cyclic-GMP phosphodiesterase (14, 15). The rd10 retinal degeneration is slower than the rate of degeneration in the most widely studied model of recessive retinal degeneration, the rd1 mouse, which loses the majority of photoreceptors by P15-P20. In rd10 mice rod loss begins at P18, and peaks around P25, so that the major phase of rod loss does not overlap with terminal differentiation of photoreceptors (16). The rd10 mouse model is amenable to gene therapy (17, 18) and antioxidant treatments have been shown to slow rod loss in this mouse model (19). In addition, rearing in conditions of dim light has been shown to slow the rate of retinal degeneration, extending the window of opportunity for therapeutic treatment (17).

Here, we investigate the effects of AAV-mediated expression of RdCVF and RdCVFL. These studies use two routes of viral vector administration: systemic injection of AAV9 via the tail vein at P1, and intravitreal injection at P15. Early systemic injection allows for onset of expression of the transgene encoded by the AAV vector at an early timepoint in the course of the degeneration, before the major phase of rod cell death and safely within the window of opportunity for evaluating the effect of expression of the transgene on rod and cone degeneration. Systemic delivery is not a clinically relevant mode of delivery to the retina, however, as many other tissues are simultaneously infected, and the immune responses represent a major bather to this approach. Therefore we also investigated the effects of intravitreal injection (a commonly used technique for intraocular delivery) of a novel variant of AAV called 7m8, which transduces photoreceptors from the vitreous (20).

We show here that expression of the two isoforms of RdCVF has positive, contrasting effects on rod and cone survival. Increased expression of RdCVF via systemic and intravitreal injections led to structural and functional rescue of cone photoreceptors, but had little effect on rods. RdCVFL on its own did not significantly rescue cones, although coexpression of RdCVF and RdCVFL increased the observed rescue effect. In contrast, expression of RdCVFL early in the course of the disease in dark reared rd10 animals prolonged rod function, increased levels of rhodopsin and decreased the byproducts of cellular oxidative stress.

These results indicate that RdCVF and RdCVFL protect photoreceptors through separate complementary mechanisms and show proof-of-concept for a widely applicable viral vector-mediated gene therapy that may be able to prolong vision in patients suffering from a variety of rod-cone dystrophies, independent of the underlying mutation.

Methods

Animals

C57Bl/6J rd10 and P23H mice were obtained from The Jackson Laboratories (Bar Harbor, Me.) and raised in a 12 hour light-dark cycle unless moved to a dark box for dark-rearing. All experiments were conducted in accordance with the ARVO Statement for the Use of Animals in Ophthalmic and Vision Research and the guidelines of the Office of Laboratory Animal Care at the University of California, Berkeley, Calif.

Production of Viral Vectors

AAV vectors carrying cDNA encoding mouse-RdCVF, RdCVFL or eGFP were produced by the plasmid co-transfection method (31). Recombinant AAV was purified by iodixanol gradient ultracentrifugation and heparin column chromatography (GE Healthcare, Chalfont St Giles, UK). The viral eluent was buffer exchanged and concentrated with Amicon Ultra-15 Centrifugal Filter Units in PBS and titered by quantitative PCR relative to a standard curve.

Agarose Sectioning and Confocal Microscopy

Retinas were freshly dissected and immediately placed in 4% paraformaldehyde overnight at 4° C. Relief cuts were made and whole retinas were embedded in 5% agarose. 150 μm transverse sections were cut on a vibratome (VT 1000S, Leica Microsystems). The sections were then mounted with Vectashield mounting media (Vector Laboratories, Burlingame Calif.) onto slides for confocal microscopy (LSM710, Carl Zeiss; Thornwood, N.Y.).

Intravascular Injections.

Postnatal day-1 pups were immobilized, and an operating microscope was used to visualize the tail vein. 10 μl of vector solution was drawn into a 3/10 cc insulin syringe. The 30-gauge needle was inserted into the vein, and the plunger was manually depressed. A total of $5 \times 10^{11}$ DNase resistant particles were injected. A correct injection was verified by noting blanching of the vein. After the injection, pups were allowed to recover for several minutes on a 37° C. heating pad prior to being returned to their cages.

Intravitreal Injections

Mice were anesthetized with ketamine (72 mg/kg) and xylazine (64 mg/kg) by intraperitoneal injection. A 30½-gauge disposable needle was passed through the sclera, at the equator and posterior to the limbus, into the vitreous cavity. A total of $5 \times 10^{10}$ DNase resistant particles in a one μl volume was subsequently injected into the vitreous cavity with direct observation of the needle directly above the optic nerve head. Contralateral control eyes received vectors carrying the gene encoding GFP or PBS.

Dark Rearing

Dark-reared mice were born and reared under dim red light in light-safe boxes, which were only opened for brief periods for animal husbandry, which was done under red light. Animals were transported to and from the box for experiments in covered cages.

qRT-PCR

Animals were humanely euthanized by $CO_2$ overdose and cervical dislocation. One retina was collected from each mouse in each experimental condition (n=5). RNA was extracted from each retina separately (RNeasy micro kit, Qiagen, Valencia, Calif.) and subjected to DNase digestion, and the resulting RNA was used to create cDNA. The housekeeping gene glyceraldehyde-3-phosphate dehydrogenase (GAPDH) was used as an internal control, and no-RT controls without reverse transcriptase were used to confirm the absence of genomic DNA. qRT-PCR was performed on samples using validated primers for RdCVF or rhodopsin. mRNA levels were determined using the relative standard curve method of qRT-PCR using a WT cDNA standard curve and are expressed as percent WT. Individual samples were run in triplicate as technical replicates.

Fundus Photography

Fundus imaging was performed with a fundus camera (Micron II; Phoenix Research Labs Inc., Pleasanton, Calif.) equipped with a filter to monitor GFP expression in live, anesthetized mice. After application of proparacaine, pupils were dilated for fundus imaging with phenylephrine (2.5%) and atropine sulfate (1%).

ERGs

Mice were dark-adapted for 2 hours and then anesthetized, followed by pupil dilation. Mice were placed on a 37° C. heated pad and contact lenses were positioned on the cornea of both eyes. A reference electrode was inserted into the forehead and a ground electrode in the tail. For an examination of retinal function under scotopic conditions ERGs were recorded (Espion E2 ERG system; Diagnosys LLC, Littleton, Mass.) under flash intensities ranging from $-3$ to 1 log cd·s/m$^2$ on a dark background. Each stimulus was presented in series of three flashes. For recording of photopic ERGs mice were initially exposed to a rod saturating background for 10 minutes. Stimuli ranging from $-0.9$ to 1.4 log cd·s/m$^2$ were presented 20 times on a lighted background. Flicker ERGs were acquired following presentation of a 30 Hz stimulus on a rod-saturating background. Stimulus intensity and timing were computer controlled. Data were analyzed with MatLab (v7.7; Mathworks, Natick, Mass.). ERG amplitudes were compared using a student's t-test.

Mosaic Acquisition and Cone Quantification

Retinal wholemounts were blocked overnight using normal donkey serum (Jackson ImmunoResearch Laboratories; West Grove, Pa.) 1:20 in PBS containing 0.5% BSA 0.1% Triton X-100, and 0.1% Azide (PBTA) at 4° C. and placed on a rotator for continuous agitation. Antibody cocktails containing goat-anti-S-Opsin (1:100; Santa Cruz Biotechnologies; Santa Cruz, Calif.), rabbit-anti-M/L-opsin (1:500; Chemicon International; Temecula, Calif.), and mouse-anti-Rhodopsin (1:100; gift from Dr. Robert Molday, University of British Columbia) were then added to a solution of PBTA and incubated for 2 days. Retinal preparations were then washed in PBTA 3×15 mins and 1× hr and subsequently corresponding secondary fluorophores were added and incubated overnight at 4° C. Finally, samples were rinsed, mounted, and coverslipped in Vectashield (Vector Labs; Burlingame, Calif.). Images of mouse retina were viewed and collected using an Olympus Fluoview 1000 laser scanning confocal microscope (Center Valley, Pa.) using a 40× UPlanFLN (N.A. 1.3) oil immersion lens. An automated stage (Applied Scientific Instrumentation: Eugene, Oreg.) was employed to capture optical sections at 1 μm intervals in the z-axis and pixel resolution of 1024×1024 in the x-y direction. These files were then used to create maximum intensity projections using the bio-image analysis software, Imago (Santa Barbara, Calif.). Digital images were captured with 20% overlap among individual images, and the resulting in ~300-400 images montaged using Imago. Cone counting was subsequently performed using Imaris software (Bitplane AG, Zurich, Switzerland) and custom software written in Python.

TBARS Assay

Malondialdehyde (MDA) concentrations were determined using a TBARS assay (Cayman Chemical Company, Ann Arbor, Mich., USA). Three retinas were pooled for each condition for each assay, and the assay was repeated 3 times. A total of 25 mg of sonicated retinal tissue was used for each assay. Retinas were sonicated in lysis buffer containing a proteinase inhibitor cocktail, then centrifuged. Supernatant was used for the TBARS assay, which was performed following manufacturer's instructions, with technical replicates prepared in triplicate. A standard curve was prepared using MDA samples of known concentration, and sample MDA concentrations were determined against the resulting curve.

Statistics

Two-tailed Student's paired or unpaired t-test was used for comparisons of experimental groups. A P value of less than 0.05 was considered statistically significant, and is indicated by an asterisk. P values less than 0.01 are indicated by a double asterisk. Error bars indicate standard deviation.

Results

Systemic Delivery of AAV92YF Via Tail Vein Injections at P1.

We examined the therapeutic effects of early RdCVF and RdCVFL delivery by intravenous (tail vein) injection of a self-complementary AAV9 vector with two tyrosine-to-phenylalanine mutations (AAV92YF). Intraocular injections into the developing eye are impractical in the initial postnatal week, however, AAV92YF has been shown to cross the blood-retina barrier when injected into the tail vein at P1, leading to high levels of gene expression across the retina (21). Systemic delivery leads to onset of expression in the retina significantly earlier in development, before significant numbers of rods are lost. AAV92YF with a ubiquitous CAG promoter driving expression of GFP (AAV92YF-scCAG-GFP) resulted in early retinal expression, which was visible in retinal flatmounts at P8 and by in vivo fundus imaging immediately after eye opening at P15. Fundus images at P35 showed strong GFP expression across the retina. Retinal flatmounts revealed that large numbers of photoreceptors were transduced. At P35 GFP expression was observed in all retinal layers, in ganglion cells, Müller glia, amacrine cells, and photoreceptors, as well as RPE. A similar pattern of widespread and strong expression, which was easily visible without immunolabeling, was observed in WT and rd10 retinas. qRT-PCR performed on mRNA collected from rd10 mice raised in a normal light-dark cycle injected at P1 with AAV92YF-scCAG-RdCVF, AAV92YF-scCAG-RdCVFL, or PBS revealed that intravenous injection of the virus resulted in high levels of RdCVF expression in the retina at P35. As expected, levels of RdCVF mRNA were greatly reduced compared to WT in PBS-injected rd10 animals of the same age (5%±5% WT). In contrast, levels of expression after AAV-mediated gene delivery were comparable to endogenous RdCVF levels in WT animals (AAV92YF-RdCVF=79%±30% WT; AAV92YF-RdCVFL=59%±13% WT). Rhodopsin mRNA expression levels remained low across conditions, indicating similar rates of rod photoreceptor loss in treated and untreated animals at P35 (AAV92YF-RdCVF=8%±3% WT; AAV92YF-RdCVFL=1%±1% WT; PBS 6%±1% WT).

Transgene expression from AAV-mediated delivery is dose dependent. Animals injected with 2E+11, 5E+11 or 1E+12 viral particles of AAV92YF-scCAG-GFP and imaged one month post-injection showed that GFP levels increased with higher viral titer. Additionally, qRT-PCR from animals injected with a range of AAV92YF-scCAG-RdCVF titers showed that RdCVF expression increased with the injection of higher numbers of viral particles.

Effect of Injection of AAV92YF.scCAG.RdCVF on Cone Function.

Mice were injected intravenously with AAV92YF-scCAG-RdCVF at P1 and subsequently raised in a normal light-dark cycle. Photopic electroretinograms (ERGs) were then measured to determine the effect of RdCVF expression on cone function. Representative ERG traces illustrate the improved waveform and amplitude of ERGs recorded from AAV92YF-scCAG-RdCVF-injected eyes compared to injections of AAV92YF-scCAG-RdCVFL, AAV92YF-scCAG-GFP or PBS. AAV92YF-scCAG-mediated expression of RdCVF resulted in significantly higher amplitude photopic ERG b-waves (97.1±10.67 μV) compared to animals injected with AAV92YF-scCAG-RdCVFL (46.7±6.4 μV, $p<0.005$) AAV92YF-scCAG-GFP (46.6±14.9 μV, $p<0.01$) or PBS (56.5±4.64 μV, $p<0.01$). WT b-wave amplitudes were 156.6±11.4 μV. ERG's were recorded from 5 animals for each condition. Data are presented as mean±SD. Photopic flicker ERG's were also recorded as a measure of cone function. Representative flicker ERG traces illustrate improved amplitude and waveform compared to GFP-injected animals.

Rescue of the photopic ERG is dose dependent, indicating that a necessary level of RdCVF expression must be achieved for significant rescue to occur. While ERG amplitudes were slightly increased with injection of E+11 vg, the difference was not significantly different, while injection of E+12 vg resulted in higher ERG amplitudes.

Transgene expression is long-lasting, with GFP expression in AAV9-scCAG-GFP injected animals readily visible in retinal flatmounts imaged one year after injection. In rd10 animals injected with AAV92YF-scCAG-RdCVF, qRT-PCR reveals elevated levels of RdCVF one year after injection.

Cone Densities in Animals Injected with AAV92YF.scCAG.RdCVF.

Automated counting of immune-fluorescent labeled cone outer segments was used to quantify cone survival. Entire retinas from animals previously used for ERG recording were flat mounted and stained with antibodies against S-opsin (blue labeling) and M/L-opsin (red labeling). High resolution 40× z-stack images were collected across the entire retina, registered and stitched together to create mosaics. Mosaics of retinal flatmounts revealed higher numbers of cones labeled with both S- and M/L-opsin in whole flatmounts from animals injected with AAV92YF-scCAG-RdCVF. Higher numbers of surviving cones of both types are apparent in higher resolution images near the optic nerve head, the region of the retina with most severe degeneration. Automated quantification of cone densities in AAV92YF-scCAG-RdCVF and PBS injected retinas revealed significantly higher numbers of both S- and M/L-cones per mm$^2$ in treated eyes. S-cone densities were: RdCVF-treated eyes: 5573±211/mm$^2$; PBS-treated eyes: 2,961±917/mm$^2$; p<0.01, WT cones: 7446±868/mm$^2$. M/L-cone densities were: RdCVF-treated eyes: 8755±1572/mm$^2$; PBS-treated eyes: 2682±293/mm$^2$; p<0.01; WT cones 9761±784/mm$^2$.

Effect of Systemic Injection of AAV92YF-scCAG-RdCVFL.

Animals were raised in the dark to slow the rate of rod loss and allow for onset of RdCVFL expression in rods before apoptosis. Reducing light exposure slowed the rate of photoreceptor degeneration as shown previously (17). Mice were injected at P1 with AAV92YF-scCAG-RdCVFL, AAV92YF-scCAG-GFP or PBS (n=6 each group). Scotopic full-field ERGs were recorded on a weekly basis. Recordings from the highest intensity light stimulus made 3, 4 and 5 weeks after injection revealed a smaller loss of a-wave amplitude at weeks 3 and 4, but this amelioration was no longer apparent at 5 weeks. The difference was statistically significant (p<0.05) only at 4 weeks post-injection. A more detailed analysis was performed on a second litter of mice injected with AAV92YF-scCAG-RdCVFL or PBS. In this group, four weeks after injection, the most significant differences in a-wave amplitudes were noted at lower light intensities (−1 and −2 log cd·s/m$^2$). Representative ERG traces illustrate preservation of the a-wave and b-wave amplitude in animals injected with AAV92YF-scCAG-RdCVFL compared to control animals injected with GFP or PBS. ERG recordings of the photopic ERG revealed a delay in the decrease of the cone ERG in RdCVFL-expressing eyes that was most noticeable 5 weeks after injection, but this difference was not statistically significant.

qRT-PCR on Rhodopsin mRNA in Dark Reared Animals Injected Systemically with AAV92YF-scCAG-RdCVFL.

qRT-PCR performed on mRNA collected from P28 animals injected with AAV92YF-RdCVFL, GFP, or RdCVF at P1 and raised in complete darkness revealed an increase in rhodopsin mRNA levels in animals injected with AAV92YF-RdCVFL (82%±21% WT, p<0.05), but not PBS (56%±6% WT), AAV92YF-GFP (59%±15% WT), or AAV92YF-RdCVF (57%±16% WT). These results, together with the rhodopsin mRNA levels measured in animals raised in a normal light-dark cycle, indicate the importance of RdCVFL delivery during a short window of opportunity for the effects of expression to be observed in this relatively rapid model of retinal degeneration, which begins to lose photoreceptors in the first few weeks of life, as no effect on levels of rhodopsin mRNA were observed in animals injected with AAV92YF-RdCVFL and raised in the light.

Measurement of Lipid Peroxidation.

A thiobarbituric acid reactive substances (TBARS) assay was used to determine levels of the lipid peroxidation byproduct malondialdehyde (MDA) in retinas treated with AAV92YF-scCAG-RdCVFL, AAV92YF-scCAG-RdCVF, AAV92YF-scCAG-GFP or PBS. The test was performed on three pooled retinas and was repeated three times. MDA levels were decreased by 18%±0.9% in RdCVFL-treated eyes compared to untreated eyes.

Intravitreal Injection of the Novel Viral Variant 7m8.

We characterized the viral tropism and expression pattern of the novel viral variant 7m8 in WT and rd10 mice after intravitreal injection at postnatal day 15 (P15). 7m8 is a variant of AAV2 developed to transduce the outer retina following intravitreal injection (20). Importantly, this variant transduces photoreceptors without subretinal injection, which has been shown to cause injury response and release of trophic factors (22). Intravitreal injections of a self-complementary 7m8 vector encoding GFP at P15 resulted in strong expression by one week after injection which was also clearly visible in fundus images at P45. Flatmounted retinas showed that large numbers of photoreceptors are transduced by 7m8. Confocal imaging of retinal cross sections revealed GFP expression in cells lying in the ganglion cell layer (GCL), inner nuclear layer (INL) and outer nuclear layer (ONL) in WT and rd10 mice The level of RdCVF expression following injection of 7m8 was evaluated by quantitative Real-Time Polymerase Chain Reaction (qRT-PCR). mRNA levels in P45 rd10 mice injected with the viral vectors encoding RdCVF, RdCVFL, or GFP were quantified. As expected, levels of RdCVF mRNA were reduced in control GFP-injected rd10 mice compared to WT (4%±1% WT). Intraocular injection of 7m8-scCAG-RdCVF or 7m8-scCAG-RdCVFL at P14 resulted in higher levels of RdCVF mRNA. Levels were 127%±35% WT in animals injected with 7m8-scCAG-RdCVF, and 91%±10% WT in 7m8-scCAG-RdCVFL-injected animals. Rhodopsin levels were uniformly low in all retinas measured (RdCVF=3%±1% WT; RdCVFL=1%±1% WT; PBS 1%±1% WT). Data are presented as mean+SD with an n=5 animals for each condition.

Effects of Expression of RdCVF and RdCVFL on Cone Structure and Function.

We next examined the effect of intraocular injection of 7m8 encoding RdCVF and RdCVFL on cone rescue in dark-reared rd10 mice. Injection of 7m8-scCAG-RdCVFL at P14 resulted in a small statistically insignificant increase in the amplitude of the photopic ERG b-wave (74±4.8 µV) compared to PBS- (65±5 µV) or GFP-injected (69±7.3 µV) eyes. Injection of 7m8-scCAG-RdCVF significantly increased the amplitude of the photopic ERG b-wave amplitude (89±7.9 µV, p<0.05) compared to GFP or PBS injected eyes. Co-injection of 7m8-scCAG-RdCVF and 7m8-scCAG-RdCVFL resulted in greater rescue of the photopic ERG, which was 53% higher than untreated eyes (99.75±5.7 µV, p<0.01) and was 17% higher than RdCVF alone (p<0.05). In all animals, one eye was injected with 7m8-scCAG-GFP or PBS as an internal control.

Cone Labeling in Eyes Injected with 7m8-scCAG-RdCVF.

Anti-S and M/L-opsin antibodies were used to label cone populations in 7m8-scCAG-RdCVF or 7m8-scCAG-GFP-injected eyes, and high resolution 40× image mosaics were created. Labeling revealed increased numbers of cones, most notably in central areas of the retina, near the optic nerve head. Automated quantification of labeled cones across the entire retina revealed an increase in cones expressing S- and M/L-opsin in 7m8-scCAG-RdCVF expressing eyes (S-cones: 1644±436 p<0.05, M/L-cones: 2205±264, p<0.05) compared to contralateral 7m8-scCAG-GFP injected eyes (S-cones: 1254±326, M/L-cones 1112±419).

Effects of Expression of RdCVF and RdCVFL in the P23H Mouse.

7m8 was next used to deliver RdCVF or RdCVFL in the homozygous or heterozygous P23H mouse, a model of dominant retinitis pigmentosa. Quantification of ERG recordings showed that injection of 7m8-scCAG-RdCVF resulted in an increase of the photopic ERG amplitude compared to PBS-injected homozygous P23H/P23H mice (RdCVF: 39±15.7 µV, PBS: 19±11.3 µV, n=6, P<0.01). In heterozygous P23H/+ mice, injection of 7m8-scCAG-RdCVF resulted in an increase in the amplitude of photopic ERG recordings up to 4 months after treatment, compared to control, GFP treated contralateral eyes. (One month post-injection, RdCVF: 175±21.4 µV vs. PBS: 107±17.2 µV, 4 months post-injection, RdCVF: 71.5±18 µV vs. PBS: 45±15.6 µV, 6 months post-injection RdCVF: 23.8±14.9 µV vs. PBS: 18±10.4 µV.). In contrast, treatment with RdCVFL did not result in any significant change in the amplitude of photopic ERG recordings at any of the time points measured. One month post-injection, RdCVFL: 135±47.3 µV vs. PBS: 120.25±53.7 µV, 4 months post-injection, RdCVFL: 72±38 µV vs. PBS: 72.8±45.2 µV, 6 months post-injection RdCVFL: 47.2±55.8 µV vs. PBS: 31±32 µV.)

Conclusion

The inventors have demonstrated the efficacy of AAV vectors as a delivery strategy for RdCVF, and show that expression of RdCVF is a promising approach to delaying the loss of cones in patients with rod-cone dystrophy.

These results demonstrate, for the first time, functional photoreceptor rescue in the retina using delivery of AAV via intravascular injection.

Similar to systemic delivery of AAV92YF, intraocular injections of 7m8 encoding RdCVF rescued cone function and prolongs cone survival. Finally, the rescue effects observed after intravitreal administration of 7m8-scCAG-RdCVF were accentuated by the co-administration of 7m8-scCAG-RdCVFL, suggesting potential for a co-expression gene therapy strategy tapping into the synergistic activities of RdCVF and RdCVFL.

In summary, these experiments support the role of Nxnl1 as a bifunctional gene encoding two isoforms of RdCVF with different activities in the retina. RdCVF is shown here to support cone survival, while RdCVFL has little direct effect on cones, but protects rod function through thio loxidoreductase activity.

Example 2: Combination of RdCVF and RdCVFL Results in a Synergistic Effect

The following constructs have been produced and introduced into an AAV2 vector. The proviral plasmid p618 and its elements are described in international patent application published as WO2012158757A1 and in publication (33).
2×RdCVF: Plasmid p857 and AAV CT-39

P857/CT39 was designed to increase the level of expression of RdCVF as compared to CT-37 (RdCVF-stuffer) to achieved sufficient cone protection in patients suffering from retinitis pigmentosa (RP).
RdCVF-RdCVFL: Plasmid p853 and AAV CT-35

This vector is able to co-express the short and long isoform of RdCVF.

These vectors were used to successfully express the RdCVF and/or RdCVFL proteins in pig retinal pigmented epithelial (RPE) cells. The protective effects of these cultures were evaluated in cone-enriched cultures form chicken embryos and were highly satisfactory.

The constructs were also tested for their protective effect on cones of the rd1 mouse after subretinal injection. A significant increase in the density of cones was observed (see FIG. 3).

In conclusion, the inventors have shown that the combination of the short and long isoforms of the NXNL1 gene, RdCVF and RdCVFL, in a single expression vector provides a synergistic effect in enhancing cone viability in situ in the retina.

The combination according to the present invention is useful for treating and/or preventing cone degeneration and other neuronal degeneration.

Example 3: RdCVFL Expression in Cone Photoreceptors Protects Cone Photoreceptors Against Oxidative Stress Example 3 corresponds to the experimental data published by the inventors in the following publication:
Mei et al., Antioxid Redox Signal. 2016 May 12. [Epub ahead of print]
The Thioredoxin Encoded by the Rod-Derived Cone Viability Factor Gene Protects Cone Photoreceptors Against Oxidative Stress.
(34 in the list of references below, incorporated by reference)

In this Example, the inventors have found that the cones express only one of the two Nxnl1 gene products, the thioredoxin RdCVFL. Administration of RdCVFL to the mouse carrying a deletion of the Nxnl1 gene in cones reduces the damage produced by oxidative stress. Silencing the expression of RdCVFL in cone-enriched culture reduces cell viability, showing that RdCVFL is a cell-autonomous mechanism of protection.

Example 4: Injection of AAV2-(RdCVF-RdCVFL) Prevents the Loss of Visual Acuity of the Rd10 Mouse a Recessive Model of Retinitis Pigmentosa Methods
Animals C57Bl/6N and rd10 mice were obtained from Charles River laboratories and The Jackson Laboratories (Bar Harbor, Me.) respectively and raised in a 12 hour light-dark cycle. All experiments were conducted in accordance with the ARVO Statement for the Use of Animals in Ophthalmic and Vision Research and the guidelines of the Office of Laboratory Animal Care at the University of California, Berkeley, Calif.

Production of Viral Vectors

AAV vectors carrying cDNA encoding human-RdCVF, RdCVFL or eGFP were produced by the plasmid co-transfection method. Recombinant AAV was purified by iodixanol gradient ultracentrifugation and heparin column chromatography (GE Healthcare, Chalfont St Giles, UK). The viral eluent was buffer exchanged and concentrated with Amicon Ultra-15 Centrifugal Filter Units in PBS and titered by quantitative PCR relative to a standard curve.

Intravitreal Injections

Mice were anesthetized with ketamine (72 mg/kg) and xylazine (64 mg/kg) by intraperitoneal injection. A 30½-gauge disposable needle was passed through the sclera, at the equator and posterior to the limbus, into the vitreous cavity. A total of 5×10¹⁰ particles in a 1 µl volume were subsequently injected into the vitreous cavity with direct observation of the needle directly above the optic nerve head. Contralateral control eyes received vectors carrying the gene encoding GFP or PBS.

Optomotor Response

Visual acuities of treated and untreated eyes were measured using optomotory Cerebral Mechanics Inc. Canada, and OptoMotry™, 1.77 system, by observing the optomotor responses of mice to rotating sinusoidal gratings. Briefly, mice reflexively respond to rotating vertical gratings by moving their head in the direction of grating rotation. The protocol used yields independent measures of the acuities of right and left eyes based on the unequal sensitivities of the two eyes to pattern rotation: right and left eyes are most sensitive to counter-clockwise and clockwise rotations, respectively. A double-blind procedure was employed, in which the observer was "masked" to both the direction of pattern rotation, to which eye received the treatment and which eye received AAV-RdCVF or AAV2-RdCVF-RdCVFL and AAV2-GFP. Briefly, each mouse was placed on a pedestal located in the center of four inward facing LCD computer monitors screens and was observed by an overhead infrared video camera with infrared light source. Once the mouse became accustomed to the pedestal a 7 sec trial was initiated by presenting the mouse with a sinusoidal striped pattern that rotates either clockwise or counterclockwise, as determined randomly by the OptoMotry™ software. Involuntary reflex head tracking responses are driven by the left (clockwise rotations) and right (counter-clockwise rotations) eyes, respectively. Contrast sensitivity was measured at a spatial frequency of 0.042 cycles/degree and at a speed of rotation of 0.5 Hz. In order to assess visual acuity, gratings had a constant contrast of 100% and initial stimulus was a 0.042 cycles/degree. Using a staircase paradigm the program converges to measures of the acuities or contrast sensitivity of both eyes defined as the spatial frequency or % contrast yielding ≥70% correct observer responses. Acuity was defined as the highest spatial frequency yielding a threshold response. Similarly, contrast sensitivity was defined as 100 divided by the lowest percent contrast yielding a threshold response. While this protocol permits the separation of right and left eye sensitivities, the contralateral eye is not 'blind' to the stimulus.

Results:

Subretinal injection of AAV2-RdCVF-RdCVFL prevents loss of visual acuity more extensively than AAV2-RdCVF.

We compared the action of an AAV2 expressing for RdCVF (CT37) to another one expressing both RdCVF and RdCVFL (CT35). The measurement of visual of the rd10 mouse acuity using optokinetics nystagmus demonstrates that the combination of RdCVF+RdCVFL (FIG. 4A) has a more pronounced protective effect than RdCVF (FIG. 4B). When translated into the loss of central vision in patients suffering from retinitis pigmentosa, the delay in the loss of visual acuity of RdCVF+RdCVFL corresponds to 44 years of prevention of blindness.

REFERENCES

Throughout this application, various references describe the state of the art to which this invention pertains. The disclosures of these references are hereby incorporated by reference into the present disclosure.

1. Buch H et al. Prevalence and causes of visual impairment and blindness among 9980 Scandinavian adults: the Copenhagen City Eye Study. *Ophthalmology.* 2004; 111(1):53-61.
2. Bramall A N, Wright A F, Jacobson S G, McInnes R R. The genomic, biochemical, and cellular responses of the retina in inherited photoreceptor degenerations and prospects for the treatment of these disorders. *Annu Rev Neurosci.* 2010; 33(1):441-472.
3. Punzo C, Kornacker K, Cepko C L. Stimulation of the insulin/mTOR pathway delays cone death in a mouse model of retinitis pigmentosa. *Nat Neurosci.* 2009; 12(1): 44-52.
4. Léveillard T et al. Identification and characterization of rod-derived cone viability factor. *Nat Genet.* 2004; 36(7): 755-759.
5. Mohand-Said S et al. Normal retina releases a diffusible factor stimulating cone survival in the retinal degeneration mouse. *Proc Natl Acad Sci USA.* 1998; 95(14):8357-8362.
6. Mohand-Said S et al. Photoreceptor transplants increase host cone survival in the retinal degeneration (rd) mouse. *Ophthalmic Res.* 1997; 29(5):290-297.
7. Mohand-Said S, Hicks D, Dreyfus H, Sahel J-A. Selective transplantation of rods delays cone loss in a retinitis pigmentosa model. *Arch Ophthalmol.* 2000; 118(6):807-811.
8. Wang X W, Tan B Z, Sun M, Ho B, Ding J L. Thioredoxin-like 6 protects retinal cell line from photooxidative damage by upregulating NF-kappaB activity. *Free Radic Biol Med.* 2008; 45(3):336-344.
9. Yang Y et al. Functional Cone Rescue by RdCVF Protein in a Dominant Model of Retinitis Pigmentosa. *Mol Ther.* 2009; 17(5):787-795.
10. Cronin T et al. The disruption of the rod-derived cone viability gene leads to photoreceptor dysfunction and susceptibility to oxidative stress. *Cell Death Differ.* 2010; 17(7):1199-1210.
11. Brennan L A, Lee W, Kantorow M. TXNL6 is a novel oxidative stress-induced reducing system for methionine sulfoxide reductase a repair of α-crystallin and cytochrome C in the eye lens. *PLoS ONE.* [published online ahead of print: 2010]; doi:10.1371/journal.pone.0015421.g008
12. Funato Y, Miki H. Nucleoredoxin, a Novel Thioredoxin Family Member Involved in Cell Growth and Differentiation. *Antioxid Redox Signal.* 2007; 9(8):1035-1058.
13. Lillig C H, Holmgren A. Thioredoxin and Related Molecules—From Biology to Health and Disease. *Antioxid Redox Signal.* 2007; 9(1):25-47.
14. Barhoum R et al. Functional and structural modifications during retinal degeneration in the rd10 mouse. *Neuroscience.* 2008; 155(3):698-713.
15. Phillips M J, Otteson D C, Sherry D M. Progression of neuronal and synaptic remodeling in the rd10 mouse model of retinitis pigmentosa. *J Comp Neurol.* 2010; 518(11):2071-2089.
16. Gargini C et al. Retinal organization in the retinal degeneration 10 (rd10) mutant mouse: A morphological and ERG study. *J Comp Neurol.* 2006; 500(2):222-238.
17. Pang J J et al. AAV-mediated gene therapy for retinal degeneration in the rd10 mouse containing a recessive PDEbeta mutation. *Investigative Ophthalmology & Visual Science.* 2008; 49(10):4278-4283.
18. Pang J J et al. Long-term retinal function and structure rescue using capsid mutant AAV8 vector in the rd10 mouse, a model of recessive retinitis pigmentosa. *Mol Ther.* 2011; 19(2):234-242.
19. Komeima K, Rogers B S, Campochiaro P A. Antioxidants slow photoreceptor cell death in mouse models of retinitis pigmentosa. *J Cell Physiol.* 2007; 213(3):809-815.
20. Dalkara D et al. In vivo-directed evolution of a new adeno-associated virus for therapeutic outer retinal gene delivery from the vitreous. *Science Translational Medicine.* 2013; 5(189):189ra76.
21. Dalkara D et al. Enhanced gene delivery to the neonatal retina through systemic administration of tyrosine-mutated AAV9. *Gene Ther.* 2012; 19(2):176-181.
22. Cao W, Wen R, Li F, Lavail M M, Steinberg R H. Mechanical injury increases bFGF and CNTF mRNA expression in the mouse retina. *Experimental Eye Research.* 1997; 65(2):241-248.
23. Hollander den A I, Black A, Bennett J, Cremers F P M. Lighting a candle in the dark: advances in genetics and gene therapy of recessive retinal dystrophies. *J Clin Invest.* 2010; 120(9):3042-3053.

24. Maguire A M et al. Safety and Efficacy of Gene Transfer for Leber's Congenital Amaurosis. *N Engl J Med.* 2008; 358(21):2240-2248.
25. Cideciyan A V et al. Human gene therapy for RPE65 isomerase deficiency activates the retinoid cycle of vision but with slow rod kinetics. *Proceedings of the National Academy of Sciences.* 2008; 105(39):15112-15117.
26. Bainbridge J W B et al. Effect of Gene Therapy on Visual Function in Leber's Congenital Amaurosis. *N Engl J Med.* 2008; 358(21):2231-2239.
27. Fridlich R et al. The Thioredoxin-like Protein Rod-derived Cone Viability Factor (RdCVFL) Interacts with TAU and Inhibits Its Phosphorylation in the Retina. *Molecular & Cellular Proteomics.* 2009; 8(6): 1206-1218.
28. Mingozzi F et al. CD8(+) T-cell responses to adeno-associated virus capsid in humans. *Nat Med.* 2007; 13(4): 419-422.
29. Manno C S et al. Successful transduction of liver in hemophilia by AAV-Factor IX and limitations imposed by the host immune response. *Nat Med.* 2006; 12(3):342-347.
30. Jacobson S G et al. Gene therapy for leber congenital amaurosis caused by RPE65 mutations: safety and efficacy in 15 children and adults followed up to 3 years. *Arch Ophthalmol.* 2012; 130(1):9-24.
31. Grieger J C, Choi V W, Samulski R J. Production and characterization of adeno-associated viral vectors. *Nat Protoc.* 2006; 1(3):1412-1428.
32. Byrne L C, Dalkara D, Luna G, Fisher S K, Clérin E, Sahel J A, Léveillard T, Flannery J G. Viral-mediated RdCVF and RdCVFL expression protects cone and rod photoreceptors in retinal degeneration. *J Clin Invest.* 2015 125(1):105-16.
33. Vasireddy, V., Mills, J. A., Gaddameedi, R., Basner-Tschakarjan, E., Kohnke, M., Black, A. H., Alexandrov, K., Maguire, A. M., Chung, D. C., Mac, H., Sullivan, L., Gadue, P., Bennicelli, J. L., French, D. L., and Bennett, J. AAV-mediated gene therapy for choroideremia: Preclinical studies in personalized models. PLoS ONE January 2013; 8(5):e61396.
34. Mei X., Chaffiol, A., Kole, C., Yang Y., Millet-Puel G., Clérin E., Aït-Ali N., Bennett, J., Dalkara D., Sahel J A, Duebel, J., Léveillard T., The thioredoxin encoded by the Rod-derived Cone Viability Factor gene protects cone photoreceptors against oxidative stress. Antioxid Redox Signal. 2016 May 12. [Epub ahead of print].

The invention claimed is:

1. An expression vector comprising a first nucleic acid encoding a short isoform of the NXNL1 gene, Rod-derived Cone Viability Factor (RdCVF) and a second nucleic acid encoding a long isoform of the NXNL1 gene, RdCVFL, wherein said expression vector is an adeno-associated virus (AAV) and wherein said short isoform of RdCVF is the short isoform of human RdCVF and wherein said long isoform is the long isoform of human RdCVFL.

2. An expression vector according to claim 1 wherein said AAV is selected in the group consisting of AAV2, AAV9 and AAV7m8.

3. A method for treating a patient suffering from a retinal degenerative disease comprising the step of administering to said patient a therapeutically effective amount of an expression vector according to claim 1.

4. A method according to claim 3, wherein said retinal degenerative disease is retinitis pigmentosa.

5. A method according to claim 3, wherein said expression vector is administered by intravenous injection or by intravitreal injection.

* * * * *